Figure 2A:
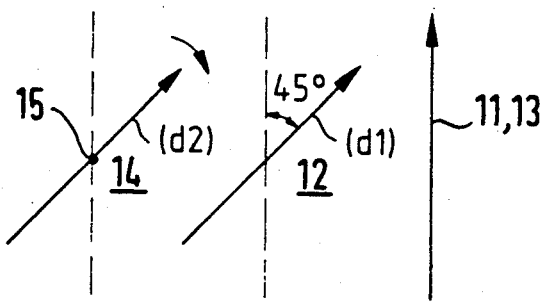

United States Patent [19]

Disch et al.

[11] Patent Number: 5,013,153

[45] Date of Patent: May 7, 1991

[54] INTERFEROMETRIC GAS COMPONENT MEASURING APPARATUS FOR SMALL GAS MOLECULES

[75] Inventors: Rolf Disch, Reute; Wolfgang Hartig, Waldkirch, both of Fed. Rep. of Germany

[73] Assignee: Erwin Sick GmbH Optik-Elektronik, Fed. Rep. of Germany

[21] Appl. No.: 383,461

[22] Filed: Jul. 20, 1989

[30] Foreign Application Priority Data

Jul. 28, 1988 [DE] Fed. Rep. of Germany ....... 3825683

[51] Int. Cl.$^5$ .............................. G01B 9/02; G01J 3/45
[52] U.S. Cl. ...................................... 356/346; 356/351
[58] Field of Search ............................... 356/346, 351

[56] References Cited

U.S. PATENT DOCUMENTS 4,320,973 3/1982 Fortunato et al.
4,718,765 1/1988 Fortunato et al. ............... 356/346
4,732,480 3/1988 Fortunato et al. ............... 356/346

FOREIGN PATENT DOCUMENTS 0091545 10/1983 European Pat. Off.
2604471 8/1976 Fed. Rep. of Germany.

*Primary Examiner*—Davis L. Willis
*Assistant Examiner*—Matthew W. Koren
*Attorney, Agent, or Firm*—Townsend and Townsend

[57] ABSTRACT

An interferometric gas component measurement apparatus has a light source (27), a measurement path (30) which contains the gas components to be measured, a polarizer (11), a double refracting plate arranged with its optical axis at 45° to the polarization direction, two doubly refracting plates (14, 20) arranged with their optical axes at 45° to one another and an analyzer (13). The light which passes through the measurement path is concentrated into an output gap (32) and reflected via a holographic concave grid (33) onto a diode row (22). The thickness of the individual plates is so selected that specific linear combinations of the thicknesses result in phase displacements between the beams polarized perpendicular to one another in the plates, with these phase displacements corresponding to the reciprocal of the quasi-periodic line splitting of selected vibration and/or rotation bands of the gas molecules of the gas components to be measured. The output signal of the diode row (22) and the output signal of a rotary position transducer (34) are applied to an electronic evaluation circuit which, at different rotational positions of the rotating plates (14, 20) determines the concentrations (C1, C2, C3) of gases present on the measurement path (30) from the signals received from the diode row (22) (FIG. 1).

6 Claims, 3 Drawing Sheets

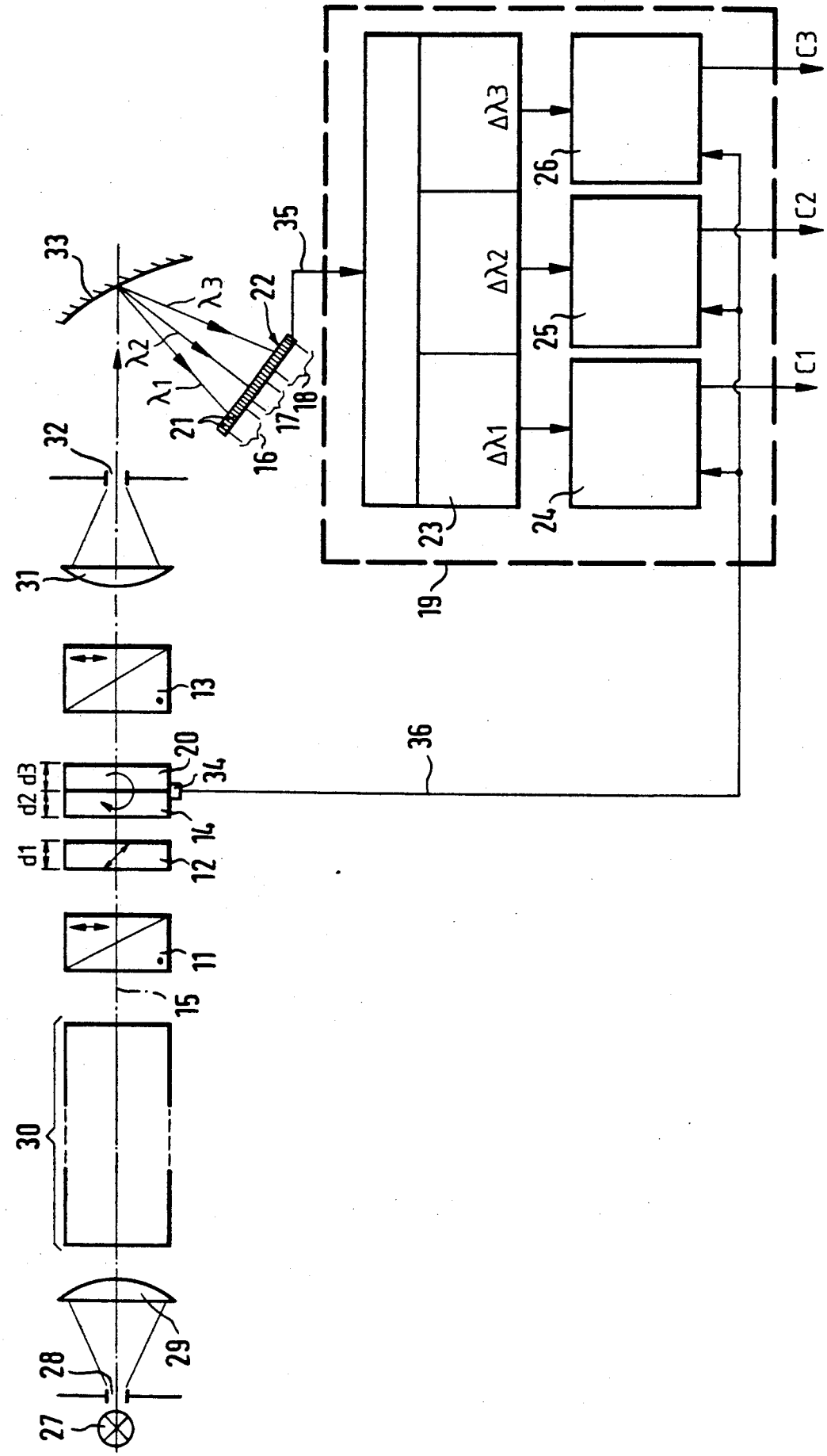

INTERFEROMETRIC GAS COMPONENT MEASURING APPARATUS FOR SMALL GAS MOLECULES

The invention relates to an interferometric gas component measurement apparatus in particular for small gas molecules of the type known from DE-OS No. 36 12 733.

Apparatus of this kind comprises:

a light source of a bandwidth which contains the absorption spectra to be used of the gases which are to be determined;

a condensor which forms an image of the light source in an input objective;

a measurement path which contains the gas components and which is illuminated by the light of the light source which enters through the input objective;

a polariser which receives the light emerging from the measurement path;

a stationary double refracting plate arranged behind the polariser and having an optical axis which includes an angle of preferably 45° with the direction of polarisation of the polariser, and a thickness such that the phase displacement between the mutually perpendicular polarised beams in the plate corresponds directly to the reciprocal of the quasi-periodic line splitting of a selected vibration and/or rotation band of the gas molecules of a gas component;

an analyser arranged behind the plate with its optical axis extending parallel to that of the polariser;

an output objective arranged behind the analyser with an output diaphragm at its focal point;

and also a diffraction grating located behind the output diaphragm, with the diffraction grating deflecting light of the selected vibrational and/or rotational band to a photoreceiver which transmits an electrical concentration signal representative of the concentration of the relevant gas component in the measurement path.

This known measurement apparatus is a polarisation interferometric correlator executed as a multi-component measurement system in accordance with DE-OS No. 26 04 471. For this purpose the polarisation interferometer is supplemented by a filter multiplex device which is formed as a polychromator with a dispersion grating and discrete detectors behind the outlet gaps which are associated with the wavelength windows. The polarisation interferometer is in particular constructed such that a plane parallel plate of a doubly refractive material is arranged between a polariser analyser pair which are orientated in parallel. With a fixed double refraction $\Delta n = n_e - n_o$ of the material the geometric thickness d of the plane parallel plate is selected such that the phase displacement between the e- and the o-beams corresponds directly to the reciprocal of the quasi periodic line splitting of the vibration and/or rotation bands of the relevant gas molecule.

In accordance with the DE-OS No. 36 12 733 a double-line of NO lying at 226 nm, a section of the $SO_2$ spectrum at 310 nm and a section of the $NO_2$ spectrum at 430 nm are simultaneously measured using a correspondingly selected plate thickness. This is possible because the plate thickness does not have to be very precisely determined and ensures good coverage of the interferometer comb with the line spectrum over wide thickness ranges of ±10%. The spectral windows are then multiplexed with the abovementioned polychromator.

The detection of several gas components with the known measuring apparatus is however only possible through the random almost identical line splitting of the three measured gas components. The method can thus not be used for any desired gas components. In claim 6 of German Offenlegungsschrift No. 36 12 733 the possibility is also mentioned of carrying out a time multiplexing of the plate thicknesses in such a way that with two double refractive plates the sum of their thicknesses is effective interferometrically when orientated in parallel and the difference of their thickness is effective interferometrically when orientated at right angles.

For the modulation of the polarisation the known arrangement uses a photoelastic modulator. A photoelastic modulator of this kind is however not entirely unproblematic with respect to the temporal constancy of the modulation, due to possible stress polarised double refraction.

The object of the present invention is now to provide an interferometric gas component measurement apparatus of the initially named kind with which two or three gas components can be detected without a restriction being necessary with respect to the selected gas components, and without having to use a photoelastic modulator. By way of example the gas component measurement apparatus of the invention should for example be able to detect the gas triple $NH_3$, NO and $SO_2$ which arise with power station burners or HF, HCl and CO which are of interest in refuse incineration.

In order to satisfy this object a first embodiment of the invention is characterised in that at least one further double refracting plate is arranged between the fixed plate and the polariser or the analyser, with the further double refracting plate having a thickness d2 such that the sum $d1+d2$ or difference $|d2-d1|$ of the thicknesses d1, d2 of the two plates produces a phase displacement between the mutually perpendicular polarised beams in the plates which corresponds to the reciprocal of the quasi-periodic line splitting of a selected vibrational and/or rotational band of the gas molecules of a further gas component; and in that a respective photoreceiver is provided for each of the two wavelength bands corresponding to the selected vibrational and/or rotational bands, with the output signals of the two photoreceivers and the angular position signal of the rotating plate being applied to an electrical evaluation circuit which, at a predetermined instantaneous angular position of the rotating plate, formes the concentration signal corresponding to the thickness of the stationary plate and the concentration signal corresponding to the sum $d1+d2$ or difference $|d2-d1|$ of the plate thicknesses.

A second embodiment is characterised in that a respective further double refracting plate is arranged between the fixed plate and the polariser, on the one hand, and also between the fixed plate and the analyser, on the other hand, with the optical axes of these further double refracting plates arranged in front of and behind the fixed plate being arranged at an angle of 45° to one another and with the plates jointly rotating about the axis of the optical system and respectively having such thicknesses d2, d3 that sums $d1+d2$; $d1+d3$ or differences $|d2-d1|$; $|d3-d1|$ of the thicknesses d1; d2, d3 of the fixed and rotating plates respectively produce a phase displacement between the mutually perpendicular polarised beams in the plates which correspond to the reciprocal of the quasi-periodic line splitting of the selected vibrational and/or rotational bands of the gas molecules of three gas components; and in that for each of the three wavelength bands which correspond to the three selected vibration and/or rotation bands a respective photoreceiver is provided, with the output signals of the three photoreceivers and the angular position signal of the rotating plates being applied to an electrical evaluation circuit which forms three concentration signals at predetermined instantaneous angular positions of the rotating plates, with the three concentration signals corresponding to three linear combinations of the thicknesses d1, d2, d3 selected from the sums d1+d2; d1+d3 and differences |d2−d1|, |d3−d1|.

The concept underlying the invention thus lies in the fact that one or two further double refracting plates should be added to the stationary double refracting plate arranged at 45° to the direction of polarisation with the further double refracting plate or plates rotating however at a predetermined frequency of typically 130 Hz about the optical axial of the optical system. In this manner at least one rotary position exists for each rotation at which the effective plate thickness formed by the two or three plates instantaneously corresponds to the thickness of the stationary plate or the sum or difference thicknesses of the two plates, or corresponds to different linear combinations of the thickness of the stationary plate and the rotating plate(s). These are pure modes of the interferometer to which fixed angular relationships belong.

In as much as the electronic evaluation circuit detects the instantaneous phase of the rotating plate or plates and executes a measurement at suitable instantaneous angular positions it is possible to continuously detect the concentration of any two or three desired gas components.

Advantageous further developments of the invention are characterised by the subordinate claims.

The invention will be described in the following by way of example and with reference to the drawings in which are shown:

FIG. 1 schematically, the optical beam path for, and also a block circuit diagram of, an interferometric gas component measurement apparatus in accordance with the invention for the measurement of three gas components, FIGS. 2a to 2e show schematic plan views of the fixed and rotating plates to illustrate the manner of operation of the embodiment for the measurement of two gas components and, FIGS. 3a to 3e show corresponding plan views and phase representations of a further embodiment for measuring three gas components.

In accordance with FIG. 1 a light source 27 having the required bandwidth is imaged by a schematically illustrated condensor 28 into an input objective 29, which in turn forms an image of the condensor aperture at infinity, so that a parallel light beam emerges from the input objective 29 which passes through a gas filled measurement path 30 and subsequently impinges on a polariser 11 which can for example be formed as Wollaston prism.

Behind the polariser 11 and a double refracting plate 14, which is described further below, a fixed double refracting plane parallel plate 12 is likewise located on the optical axis 15 of the optical system perpendicular to the latter. The optical axis of the plane parallel plate 12 is arranged at 45° to the direction of polarisation of the polariser 11. The double refracting plate 12 has a thickness d1 which is selected in a manner matched to the gas components to be measured, which will be described further below in detail with reference to FIGS. 2 and 3.

Before and behind the fixed double refracting plate 12 there are located, on the optical axis 15, two further double refracting plane parallel plates 14 and 20 with thicknesses d2 and d3 respectively. The plates 14 and 20 are rotationally fixedly coupled together by a schematically illustrated rotary coupling 37, with their optical axes displaced by 45° to one another. The plates 14 and 20 rotate about the axis 15 of the optical system. Following the plate 20 there is provided an analyser 13, the optical axis of which extends parallel to that of the polariser 11. There then follows an output objective 31 with an output gap diaphragm 32 being located at its focal point and with the inlet gap diaphragm 28 being imaged in the output gap diaphragm 32.

Behind the output gap diaphragm 32 there is located an inclined holographic concave grid 33 forming a diffraction grating with the concave grid reflecting incident light beams to a diode row 22 at somewhat different angles depending on the wavelength. The diode row comprises a plurality of individual diodes arranged in a row. The diode row 22 can for example consist of 256 individual diodes 21.

The diode row 22 and an angular position transducer 34 which is provided on the jointly rotating plates 14, 20 and which interrogates the instantaneous angular position of the plates 14, 20 are connected via lines 35 and 36 to an electronic evaluation circuit 19 which contains a diode selection circuit 23 and three lock-in amplifiers 24, 25, 26. The angular position control line 36 is connected to the control inputs of the lock-in amplifiers 24, 25, 26.

The diode selection circuit 23 respectively combines a number of individual diodes 21 into corresponding broad band photoreceivers 16, 17 and 18 and forms, by integration of the diode signals, characteristic intensity signals in the wave bands $\Delta\lambda1$, $\Delta\lambda2$ and $\Delta\lambda3$ which extend around the three wavelengths $\lambda1$, $\lambda2$ and $\lambda3$ respectively, with these three wavelengths being characteristic wavelengths for three different gas components in the measurement path 30.

The individual diodes 21 combined into the photoreceivers 16, 17 and 18 respectively thus represent bandpass filters around the wavelengths $\lambda1$, $\lambda2$ and $\lambda3$ respectively. When individual photoreceivers are used (for example in the infrared) then it is best to use interference filters.

A corresponding bandwidth can be realised around the three selected wavelengths $\lambda1$, $\lambda2$ and $\lambda3$ depending on how many individual diodes 21 can be combined into the photoreceivers 16, 17 and 18.

The lock-in amplifiers 24, 25, 26 receive the intensity signals from the wavelength bands $\Delta\lambda1$, $\Delta\lambda2$ and $\Delta\lambda3$ as an input signal and transmit concentration signals C1, C2 and C3 respectively only in angular positions of the plate pack 14, 20 which are predetermined in a quite specific manner, which will be described in detail in the following with reference to FIGS. 2 and 3.

The FIGS. 2a to 2e show the case which only one fixed plate 12 and one rotating plate 14 are provided. The rotating plate 14 could also be arranged behind the fixed plate 12. In FIGS. 2 and 3 the optical axis of the polariser 11 and of the analyser 13 is symbolised by the arrow 11, 13. The optical axes of the double refracting plates 12, 14 are respectively symbolised by an arrow to which the abbreviations (d1) and (d2) for the thickness of the relevant plate 12 and 14 respectively have been added to distinguish between the plates.

As seen in FIG. 2a the optical axis (d1) of the fixed plate 12 is arranged as an angle of 45° to the optical axis of the polariser 11 and of the analyser 13.

When now, in the course of the rotary movement of the rotating plate 14 the optical axis d2 of this plate is likewise arranged at an angle of 45° to the direction of polarisation, then in this case the thicknesses d1 and d2 are added to form a sum thickness d1+d2, so that at this instant it appears that a single plate is present with a thickness corresponding to the sum of thicknesses. A corresponding intensity signal appears on the diode row at the wavelength band $\Delta\lambda 1$. If the lock-in amplifier 24 is now activated at this instant by the angular position transducer 34 then a concentration signal C1 appears at its output which is representative for a corresponding gas component.

The total plate thickness d1+d2 should be so selected that the phase displacement between the e-beam and the o-beam (these are the polarised beams perpendicular to one another within the doubly refractive plate) corresponds precisely to the reciprocal of the quasi-periodic line splitting of the vibration or rotation bands (spectrum bands) of the gas molecule of a gas component to be measured.

Figure 2B:
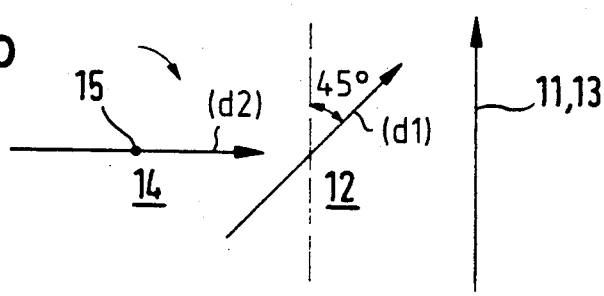

In the position of FIG. 2b the plate 14 has turned on further through an angle of 45° relative to FIG. 2a, so that the optical axis d2 of the plate 14 now stands perpendicular to the direction of polarisation. In this case the rotating plate 14 does not generate any path difference and the phase displacement of the two mutually polarised beams is determined solely by the fixed plate 12. The effective plate thickness thus corresponds at this instant to the thickness d1 of the fixed plate 12. A wavelength signal from the wavelength band $\Delta\lambda 2$ now appears on the diode row 22 in the region of the photo-receiver 17, and can be associated with a further gas component by selecting the thickness d1 such that the phase displacement between the e- and the o-beam corresponds precisely to the reciprocal of the quasi-periodic line splitting of the vibration and/or rotation bands of the gas molecule of the further gas component.

Figure 2C:
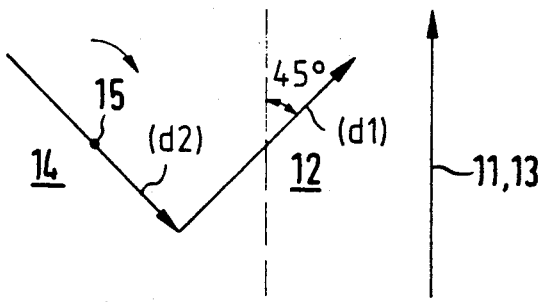

In the position of FIG. 2c the plate 14 has turned through a further 45° relative to FIG. 2b, so that the optical axes d1 and d2 of the two plates 12 and 14 are now perpendicular to one another. This corresponds to an effective total plate thickness $|d2-d1|$, so that a gas component corresponding to this absolute difference can be provided, and can be measured technically in as much as one of the further lock-in amplifiers 25 or 26 is correspondingly activated. One of the further lock-in amplifiers 25, 26 is also activated in the case of FIG. 2b at the instant when the effective plate thickness d1 is present.

Figure 2D:
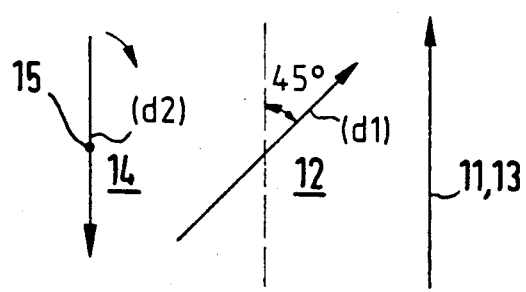

In the illustration of FIG. 2d the rotating plate 14 has turned through a further 45° so that the optical axis of the rotating plate 14 now extends parallel to the polarisation direction. In this case the effective plate thickness is again d1.

Figure 2E:
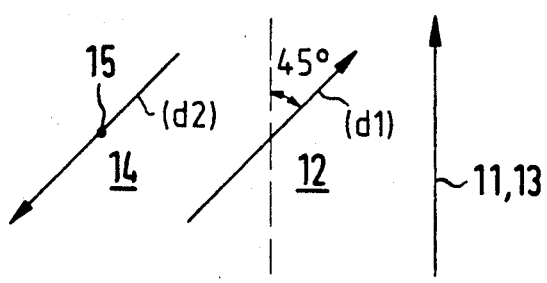

On a further rotation through 45° in accordance with FIG. 2e the optical axes d1 and d2 again extend parallel to one another, so that in the same way as in the angular position of FIG. 2a the effective plate thickness d1+d2 is again present, which can be detected to form a concentration signal C1 by a suitable control of the lock-in amplifier 24.

In FIGS. 3a to 3d the same reference numerals are used to designate parts having counter-parts in FIGS. 2a to 2e. FIGS. 3a to 3e functionally illustrate the case reproduced in FIG. 1 in which double refracting plates 14, 20 are arranged with their optical axes d2 and d3 fixed at an angle of 45° to one another, in front of and behind the fixed plate 12 respectively, in order to jointly rotate in the direction of the rotary arrow about the axis 15 of the optical system.

Figure 3A:
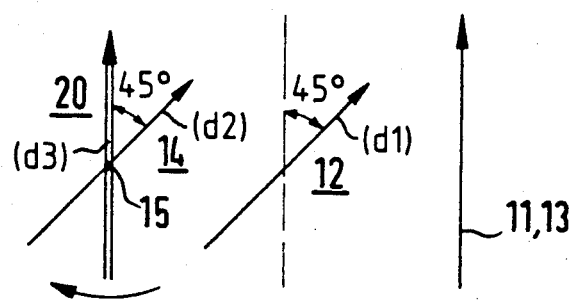

In the rotary position of the plates 14, 20 of FIG. 3a the optical axis d2 is parallel to the optical axis d1 of the fixed plate 12, while the optical axis d3 of the doubly refracting plate 20 which fixedly rotates with the plate 14 extends parallel to the polarisation direction of the polariser 11 and of the analyser 13.

In the rotary position of FIG. 3a there is thus an effective plate thickness corresponding to the sum d1+d2. This effective total thickness could be associated with a first gas component in the sense of the above explanations.

Figure 3B:
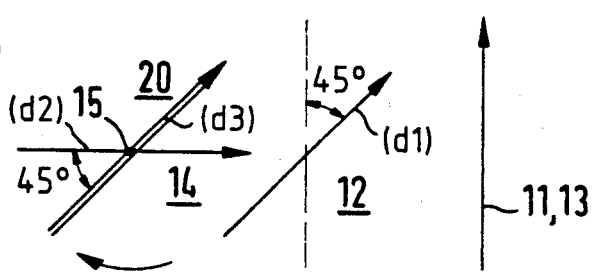

In FIG. 3b the plates 14, 20 have turned on further through an angle of 45° so that now the optical axis d2 of the rotating plate 14 extends perpendicular to the direction of polarisation, and is thus neutralised, while the optical axis d3 of the rotating plate 20 extends parallel to the optical axis d1 of the fixed plate. This corresponds to an effective total thickness d1+d3. A further gas component could be associated with this effective total thickness by selecting this sum such that the phase displacement between the e- and the o-beam directly corresponds to the reciprocal of the quasi-periodic line splitting of the vibrational and/or rotational bands of the gas molecules of a further gas component.

Figure 3C:
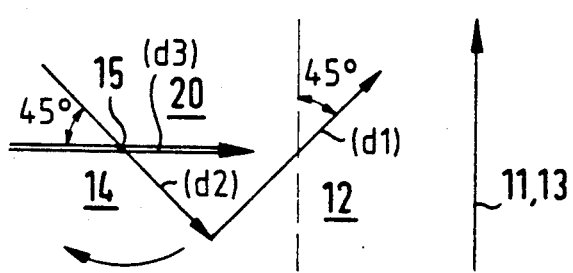

FIG. 3c shows a further instantaneous recording of the rotary positions of the plates 14, 20 and indeed turned through a further angle of 45° relative to FIG. 3b. The rotating plate 20 is now neutralised in as much as its optical axis d3 extends perpendicular to the direction of polarisation. As however the optical axes d2 and d1 are now perpendicular to one another this corresponds to an effective total plate thickness of $|d2-d1|$. This effective plate value can be associated with a specific component in the sense of the above comments.

Figure 3D:
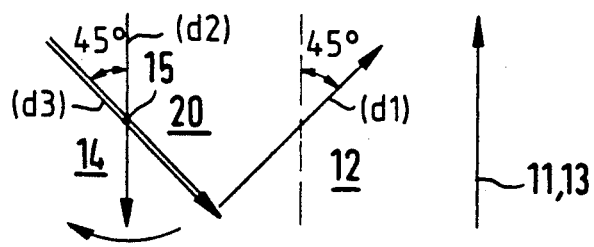

On a further 45° rotation in accordance with FIG. 3d the optical axis d2 extends parallel to the direction of polarisation while the optical axes d3 and d1 are perpendicular to one another. This results in an effective plate thickness of $|d3-d1|$. Here a suitable association with a specific gas component can also be found.

Figure 3E:
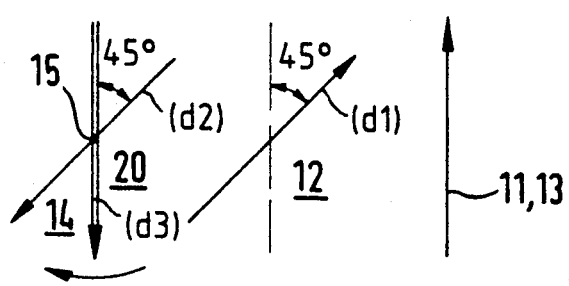

Finally, after a further 45° rotation of the plates 14, 20 the optical axes d2 and d3 extend, in accordance with FIG. 3e parallel to one another again, in similar manner to FIG. 3a, while d3 is parallel to the direction of polarisation. The effective plate thickness state in accordance with FIG. 3a has now been reached again, i.e. the effective plate thickness amounts in the rotational position of FIG. 3e to d2+d1.

The individually described combinations repeat again for the second half circles of the rotation of the rotating plates 14, 20 which are described in FIGS. 2a to 2e or 3a to 3e.

The plate thicknesses d1, d2 and optionally d3 can always be so selected that three suitable linear combinations of thicknesses d2, d3 of the rotating plates 14, 20 with the thickness d1 of the fixed plate always suit two or three desired gas components respectively. The fourth combination is then no longer freely selectable and will thus generally not be used.

The advantages of the arrangement of the invention lie in the fact that an additional polarisation modulation is unnecessary, and in the fact that the signals belonging to the gas components are present in coded form with different frequency and phase position in the output signal of the detector, in particular the diode row. A further separation takes place through different spectral windows which are uniquely associated with the absorption bands of the individual molecules.

The use of dielectric interference filters as bandpass filters under 350 nm is not unproblematic. With the required half value width of ca. 3% of the central wavelength the transmission is not better than 15%. The reproducability of the central wavelength and half value width can generally not be guaranteed by the manufacturers. It is thus of advantage to use a polychromator with a holographic concave grid 33 with a flat field in the image plane as shown in FIG. 1. A diode row 22 in accordance with CCD-ECD technology is used here as a detector. The filtering takes place by integration of the signals via selected diode ranges 16, 17 or 18 which are associated with the spectral windows. This results in bandpass filters with an approximately rectangular spectral transmission curve with polychromatic transmission values of typically 30 to 40%. The integrated diode signals are passed to the separate lock-in amplifiers 24 to 26 which are locked to the double rotational frequency of the rotating plate 14 or of the rotating plate pair 14, 20 at different phase positions. The output signals of the lock-in amplifiers 24, 25 and 26 are proportional to the gas concentrations C1, C2 and C3 that are being sought.

We claim:

1. An interferometric gas component measuring apparatus, comprising:
   a light source having a bandwidth of light which encompasses the absorption spectra to be used with the gases which are to be measured;
   an input objective and an output objective;
   a condenser which forms an image of the light source in the input objective;
   a measurement path for containing the gas components to be measured, said measurement path illuminated by light from the light source entering said measurement path through the input objective;
   a polarizer which receives the light emerging from the measurement path;
   a stationary first double refracting plate arranged between the polarizer and the output objective, said polarizer having an optical axis which includes an angle of 45° with the direction of polarization of the polarizer, and a thickness (d1) such that a phase displacement between mutually perpendicular polarized beams in the first double refracting plate corresponds directly to a reciprocal of a quasi-periodic line splitting of a selected vibration and/or rotation band of gas molecules contained in the gas component to be measured;
   an analyzer arranged between the first double refracting plate and the output objective, said analyser having an optical axis extending parallel to the optical axis of the, said output objective having an output diaphragm at its focal point;
   a diffraction grating disposed adjacent to the output diaphragm;
   a diffraction grating for deflecting light of the selected vibrational and/or rotational band to a photoreceiver which transmits an electrical concentration signal representative of the concentration of the relevant gas component in the measurement path;
   a rotatable second double refracting plate adjacent to the first double refracting plate, wherein the second double refracting plate has a thickness (d2) such that the sum (d1+d2) or difference ($|d2-d1|$) of the thicknesses (d1, d2) of the first double refracting plate and the second double refracting plate produces a phase displacement between the mutually perpendicular polarised beams in the first double refracting plate and the second double refracting plate which corresponds to a reciprocal of the quasi periodic line splitting of a selected vibrational and/or rotational band of gas molecules of a gas component;
   a first and second photoreceiver corresponding to the selected vibrational and/or rotational bands; and
   an electrical evaluation circuit, wherein output signals from the first and second photoreceivers and an angular position signal taken from the rotating second double refracting plate is applied to the electrical evaluation circuit, and at predetermined instantaneous angular positions of the rotating second double refracting plate, said electrical evaluation circuit forms a first concentration signal corresponding to the thickness (d1) of the first double refracting plate and a second concentration signal corresponding to the sum ($|d1-d2|$) or difference ($|d2-d1|$) of the first double refracting plate and second double refracting plate thicknesses.

2. A gas component measurement apparatus in accordance with claim 1, characterized in that the first, second and third photoreceivers are formed by a plurality of individual diodes arranged in a diode row said first, second and third photoreceivers, respectively, associated with a wavelength band ($\Delta\lambda_1$, $\Delta\lambda_2$, $\Delta\lambda_3$).

3. A gas component measurement apparatus in accordance with claim 2, characterized in that a diode selection circuit is connected to the diode row, said diode selection circuit producing a plurality of integrated diode signals wherein each of said integrated diode signals is outputted to a dedicated lock-in amplifier, each said lock-in amplifier being locked at different phase positions to a double-rotational frequency of the rotating second double refracting plate or of the rotating second double refracting plate and third double refracting plate pair.

4. An interferometric gas component measuring apparatus, comprising:
   a light source having a bandwidth of light which encompasses the absorption spectra to be used with the gases which are to be measured;
   an input objective and an output objective;
   a condensor which forms an image of the light source in the input objective;
   a measurement path for containing the gas components to be measured, said measurement path illuminated by light from the light source entering said measurement path through the input objective;
   a polarizer which receives the light emerging from the measurement path;
   a stationary first double refracting plate arranged between the polarizer and the output objective, said polarizer having an optical axis which includes an angle of 45° with the direction of polarization of the polarizer, and a thickness (d1) such that a phase displacement between mutually perpendicular polarized beams in the first double refracting plate corresponds directly to the reciprocal of a quasi-periodic line splitting of a selected vibration and/or rotation band of gas molecules contained in the gas component to be measured;

an analyser arranged between the first double refracting plate and the output objective said analyser having an optical axis extending parallel to the optical axis of the polarizer; said output objective having an output diaphragm at its focal point;

a diffraction grating disposed adjacent to the output diaphragm;

a diffraction grating for deflecting light of the selected vibrational and/or rotational band to a photoreceiver which transmits an electrical concentration signal representative of the concentration of the relevant gas component in the measurement path;

a second double refracting plate and a third double refracting plate arranged adjacent to the first double refraction plate and between the polarizer and the analyser, with the optical axis of the second double refracting plate and the third double refracting plate arranged at an angle of 45° to one another and with the second double refracting plate and the third double refracting plate jointly rotating about the axis of the optical system and respectively having such thicknesses (d2, d3) that sums (d1+d2; d1+d3) or differences (|d2−d1|; |d3−d1|) of the thicknesses (d1; d2, d3) of the first double refracting plate, the rotating second double refracting plate and third double refracting plate respectively produce a phase displacement between the mutually perpendicular polarised beams in the first, second and third double refracting plates which correspond to a reciprocal of the quasi-periodic line splitting of the selected vibrational and/or rotational bands of gas molecules of three gas components;

a first photoreceiver, a second photoreceiver and a third photoreceivers corresponding to the three wavelength bands which correspond to the three selected vibration and/or rotation bands;

photoreceiver; and an electrical evaluation circuit, wherein the output signals of the first, second and third photoreceivers and an angular position signal of the rotating second double refracting plate and the third double refracting plate are applied to the electrical evaluation circuit, said electrical evaluation circuit forming a first concentration signal, a second concentration signal and a third concentration signal at predetermined instantaneous angular positions of the rotating plates, with the first, second and third concentration signals corresponding to three linear combinations of the thicknesses (d1, d2, d3) selected from the sums (d1+d2; d1+d3) and difference (|d2−d1|, |d3−d1|).

5. A gas component measurement apparatus in accordance with claim 4, characterized in that the first, second and third photoreceivers are formed by a plurality of individual diodes arranged in a diode row said first, second and third photoreceivers, respectively, associated with a wavelength band ($\Delta\lambda_1$, $\Delta\lambda_2$, $\Delta\lambda_3$).

6. A gas component measurement apparatus in accordance with claim 5, characterized in that a diode selection circuit is connected to the diode row, said diode selection circuit producing a plurality of integrated diode signals ($\Delta\lambda_1$, $\Delta\lambda_2$, $\Delta\lambda_3$) wherein each of said integrated diode signals is outputted to a dedicated lock-in amplifier, each said lock-in amplifier being locked at different phase positions to a double-rotational frequency of the rotating second double refracting plate or of the rotating second double refracting plate and third double refracting plate pair.

* * * * *